United States Patent [19]

Reed

[11] 4,033,344

[45] July 5, 1977

[54] RECOVERY OF CHORIONIC GONADOTROPIC HORMONE FROM PREGNANT MARES

[76] Inventor: Jack Owen Reed, 1585-B Bergen Blvd., Leonia, N.J. 07605

[22] Filed: Apr. 28, 1975

[21] Appl. No.: 572,625

[52] U.S. Cl. .................... 128/214 R; 424/101; 260/112 B
[51] Int. Cl.² ............................................. A61M 5/00
[58] Field of Search .......... 128/1 R, 214 R, DIG. 3; 424/100, 101; 260/112 B

[56] References Cited

UNITED STATES PATENTS

| | | | |
|---|---|---|---|
| 3,457,346 | 7/1969 | Van Hell | 424/101 X |
| 3,483,867 | 12/1969 | Markovitz | 128/214 R X |
| 3,489,145 | 1/1970 | Judson et al. | 128/214 R |
| 3,579,441 | 5/1971 | Brown | 128/214 R X |
| 3,719,182 | 3/1973 | Rose | 128/1 R |
| 3,852,422 | 12/1974 | Domini | 424/100 |

*Primary Examiner*—Dalton L. Truluck
*Attorney, Agent, or Firm*—Fidelman, Wolffe & Waldron

[57] ABSTRACT

Periodic bleeding, e.g. fortnightly or weekly, of pregnant mares is carried out with return to the blood stream of the mare all cellular constituents in the withdrawn blood and also the plasma constituents having a molecular weight above about 40,000 m.w.

Optionally, the plasma constituents having a molecular weight below about 20,000 m.w. are returned as well.

The 20,000–40,000 m.w. fraction of the plasma constitutes a Chorionic Gonadotropic Hormone product of high purity.

4 Claims, No Drawings

RECOVERY OF CHORIONIC GONADOTROPIC HORMONE FROM PREGNANT MARES

The present invention relates to the recovery of pharmacologically active substances from living animals and in particular to the recovery of pharmacological active substances from pregnant mares.

It has long been recognized that pregnant mares generate relatively large quantities of hormones of considerable value to the medical arts. Urine from pregnant mares has been collected as source material for recovery of the hormone values therein.

However, not all of the pharmacologically active recoverable hormones generated in large quantities by the pregnant mare are excreted in the urine. In particular, the chorionic gonadotropic hormone (also known as pituitary-like gonadotropin) occurs in the blood serum of the pregnant mare, but this hormone is not excreted in the urine. Recovery of this hormone has traditionally involved bleeding pregnant mares to a point just short of endangering the fetus. The chorionic gonadotropic hormone has been recovered heretofore from the blood serum. However, loss of much blood is such a shock to the system of the pregnant more that a limited number of bleedings, normally not more than abut two large volume bleedings or multiple small volume bleeding is possible between the 45-90th day of pregnancy when the hormone level in the bloodstream is highest. The shock due to loss of blood is somewhat decreased if the blood withdrawn from the mare is prevented from clotting with an anticoagulant and is centrifuged to separate out the cellular elements, and the cellular elements are then returned to the mare. However, loss of substantial quantities of plasma is in and of itself, a substantial shock to the blood vascular system of the mare due to the loss of normal osmotic pressure provided by the plasma proteins.

According to practice of the present invention, more frequent large volume bleedings such as once a fortnight or even once a week can be carried out without endangering the unborn foal or otherwise harming the pregnant mare.

Briefly stated, the practice of the present invention involves bleeding the mare, thereafter separating the blood into cellular elements and plasma and returning the cellular elements to the mare.

The plasma is then subjected to molecular fractionation to remove therefrom the chorionic gonadotropic hormones. Much of the remaining plasma constituents, particularly the constituents with higher molecular weights than the gonadotropic hormones, are returned to the mare. In consequence, the mare loses only blood consituents that are quickly and readily replaced, namely the gonadotropins, any other plasma constituents having about the same molecular weight, and optionally the lower molecular weight constituents, e.g. blood sugar and salts.

The preferred practice of this invention includes the following sequence:

1. Bleeding the mare prior to pregnancy (one or more times) in order to have on hand a stock of plasma which may for example be 2,000 or 3,000 ml. To reduce the shock, the prepregnancy bleeding operation may include separation of the cellular constituents and return thereof to the mare. The plasma is placed in frozen storage with proper identification to assure return to the donor.

2. Commencing at about the 60th day of pregnancy the mare is bled weekly or bi-weekly, removing about 4 litres of blood each bleeding until about the 150th day. At each bleeding the cellular constituents are promptly separated from the plasma, suspended in saline and returned to the mare (about 2,000 ml). On the first bleeding, the stock plasma is unfrozen (also about 2,000 ml) and returned to the mare.

The gonadotropin containing plasma taken from the pregnant mare is subjected to molecular filtration to separate out the constituents having a molecular weight less than about 40,000 m.w. The separated out material contains the gonadotropins. The balance is then frozen for return to the mare at the next bleeding.

The 40,000+m.w. substances recycled back to the pregnant mare according to practice of this invention are important to the well-beng of the animal (maintenance of normal osmotic pressure in the blood vascular system). Included for example are the immunoglobulins, the lipoproteins, albumin and many other protein constituents of the blood, such material being synthesized slowly in the animal. Return of the 40,000+m.w. plasma fraction eases the metabolic demand processes of the animal, since all that must be replaced by such processes are the less than 40,000 m.w. constituents lost through the bleeding. The lower molecular weight blood constituents are, generally speaking, rapidly synthesized in the animal. In consequence, the pregnant mare recovers (from the bleeding) very rapidly and is fit for bleeding once again in just a few days. Bleeding once a fortnight or even once a week can be practiced safely.

The chorionic gonadotropic hormone is a discreet substance havng a molecular weight of about 30,000. In consequence, state of the art molecular filtration (through controlled pore size filtration membranes) can separate the plasma into a fraction retentate that contains essentially all constituents having molecular weights in excess of about 40,000 (including for example the albumin, immunoglobulins, etc. important to maintenance of the normal osmotic pressure in the blood vascular system of the mare) while the pass fraction will include ingredients having a molecular weight below about 40,000; this fraction includes the gonadotropins. The high molecular weight containing retentate fraction is, of course, that portion returned to the pregnant mare according to practice of the present invention.

An optional feature of practice according to this invention is returning to the pregnant mare the plasma constituents having less than about 20,000 m.w.

One principal advantage of the present invention is that the yield of chorionic gonadotropic hormones from each pregnant mare is increased several fold, by virtue of the more frequent large volume bleeding that now is possible. Since care and maintenance of the animal is a significant expense, such as substantial yield increase is of material consequence.

A second advantage of the present invention is that product purity is greatly enhanced over the PMS presently available to the veterinary practitioner. According to a typical prior art practice the blood obtained from a pregnant mare is allowed to clot and the serum recovered. (The gonadotropin (s) content remains dissolved in the serum.) The pregnant mare serum (PMS) is made available in vials for its gonadotropin (s) content in dosage form units. Chorionic gonadotropic hormone (s) is widely administered to domestic animals such as cattle, horses, sheep, goats, dogs, swine (by licensed veterinarians) in the treatment of breeding disorders, including functional impotence of the male and failure of the female to come into heat or conceive. Unfortunately, on occasion, administration of PMS causes anphylactoid reactions, such reaction being a serious side effect attributed to the complex (sensitizing) proteins present in the PMS.

Practice of this invention results in a gonadotropin(s) containing plasma fraction from which the high molecular weight substances (including of course many complex sensitizing proteins) have been excluded. As compared to the PMS, the molecularly fractionated product is more pure, can be expected to cause a lower incidence of anaphylactoid reactions.

A more purified product is obtained by subjecting the recovered plasma fraction (i.e. the pass fraction from the molecular filtration) to a second molecular filtration. This time the membrane passes materials having a molecular weight below about 20,000 including for example blood sugar, salts low molecular weight proteinaceous materials. The (second) retentate fraction has concentated, therein, the molecular weight 20,000 to 40,000 m.w. substances, which of course includes the gonadotropin(s). This second fraction constitutes the preferred product of this invention. It may be lyophilized (with or without an extender such as dextran) or simple hexose sugar for later use by veterinarians without still further purification. In total, the product is far more purified of objectional sensitizing substances (proteins) than the PMS material heretofore available to the art.

The pass fraction of the second molecular filtration may, of course, be discarded. Alternatively, this lower than 20,000 m.w. plasma portion may be frozen (for storage), then thawed and returned to the mare during or shortly after a next subsequent bleeding (at the same time that the higher than 40,000 m.w. plasma fraction is returned to the mare). In this alternative, the overall result is that bleeding has taken from the mare only 20,000–40,000 m.w. constituents present in the blood stream.

For further understanding of the invention, reference is now made to the following protocol and example:

SCHEDULE OF BLEEDING FOR GONADOTROPINS FROM PREGNANT MARE PLASMA

Each mare = 1,000 lbs. body weight
7.0% blood = 70 lbs. whole blood
Bleed 4 liters = 9.25 lbs. whole blood = 4,000 cc.
Plasma = 57% = 5.27 lbs. plasma = 2,280 cc.
Cells = 43% = 3.98 lbs. cells = 1,720 cc.
PROCEDURE: Have 2,000 cc. of plasma proteins ready for first pregnancy bleeding —
1. Take 4 liters of blood from left jugular vein into A.C.D. (anticoagulant, citrate, dextrose) solution.
2. Feed 2 liters of plasma proteins into right jugular vein starting with the second 1,000 cc. bleeding from the left jugular vein.
3. Run blood through Centrifuge and separate plasma from cells.
4. Immediately return all cells (approximately 1,720 cc) to donor mare w/500 cc. of Ringers Solution.
5. Pass plasma through Millipore w/(NMWL — 40,000) filters: Mark and hold Retentate No. 1 (large proteins); designate (mark) Filtrate as No. 1.
6. Pass Filtrate No. 1 through Millipore w/NMWL – 20,000 filter; collect Retentate No. 2 (contains Gonadotropins- MW — 30,000) into common receptacle (Marked Retentate No. 2) and combine with Retentate No. 2 from all other mares' plasmas processed during the same day; Mark Filtrate No. 2 (contains small molecules and electrolytes).

NOTE: Keep Retentate No. 2 vessel in ice bath throughout processing period.
7. Combine Filtrate No. 2 with Retentate No. 1, place in frozen storage (2,000 cc.) for plasma protein feedback to donor (mare) on next bleeding.
8. Retentate No. 2 contains the chorionic gonadotropins and is combined from enough donar mare to make an economical production size bath. This fraction can be frozen and in such state retains its full potency until reconstituted in saline or similar diluent.

For production purposes the frozen Retentate No. 2 fractions are thawed, combined, well mixed for homogenous distribution, and are then cryodessicated at low temperature under vacuum to produce a lyophilized powder. A small aliquot of this material is reconsititued and assayed against the most recent International Standard for potency determination. Ultimately the appropriate weight of powder is filled into dosage unit forms which in a preferred embodiment would be a two compartment glass contaner, one compartment containing the active Chorionic Gonadotropin powder while the other separated compartment contains the appropriate volume of extender liquid (a standard dosage unit for the horse is 60–150 rat units).

What is claimed is:

1. A method for recovery of chorionic gonadotropic hormone (s) from pregnant mares which comprises:
   a. large volume bleeding a pregnant mare;
   b. then separating the blood removed from said mare into cellular constituents and plasma;
   c. thereafter subjecting the plasma to molecular fractionation separating the plasma into a first plasma fraction containing substances of molecular weight in excess of about 40,000 and a second plasma fraction containing substances of molecular weight less than about 40,000 the last containing the chorionic gonadotropic hormone (s); and
   d. returning to the blood stream of the mare the cellular constituents and the first plasma fraction.

2. The method of claim 1 wherein the mare is bled at intervals not less frequent than once a fortnight during the period extendng from about the 60th day to the 150th day of her pregnancy term.

3. The method of claim 2 wherein an initial bleeding is carried out prior to commencement of pregnancy, obtaining thereby a reserve stock of plasma, such plasma stock serving for the plasma fraction returned to the mare on the occasion of the first bleeding during her pregnancy term.

4. The method of claim 1 wherein the second plasma fraction is further separated into a less than 20,000 m.w. portion and a greater than 20,000 m.w. portion, the later portion containing the chorionic gonadotropic hormone(s) therein, and wherein the less than 20,000 m.w. plasma portion is returned to the blood stream of the mare.

* * * * *